(12) United States Patent
Servidio

(10) Patent No.: US 11,737,880 B2
(45) Date of Patent: Aug. 29, 2023

(54) INTEGRATED SPRING FOR SOFT TISSUE ATTACHMENT

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 120 days.

(21) Appl. No.: 16/148,337

(22) Filed: Oct. 1, 2018

(65) Prior Publication Data

US 2019/0099273 A1  Apr. 4, 2019

Related U.S. Application Data

(60) Provisional application No. 62/567,329, filed on Oct. 3, 2017.

(51) Int. Cl.
*A61F 2/30* (2006.01)
*A61F 2/28* (2006.01)
(Continued)

(52) U.S. Cl.
CPC ........ *A61F 2/30749* (2013.01); *A61F 2/0811* (2013.01); *A61F 2/28* (2013.01);
(Continued)

(58) Field of Classification Search
CPC ................ A61F 2/30749; A61F 2/0811; A61F 2002/30566; A61F 2002/0835; A61F 2002/0847; A61F 2002/0829; A61F 2/28; A61F 2/46; A61F 2002/30565; A61F 2002/087; A61F 2002/30733; A61F 2/3877; A61F 2002/30074; A61F 2002/30011; A61F 2002/30571; A61F 2002/30329; A61F 2002/30579; A61F 2002/30985; A61F 2002/30164
See application file for complete search history.

(56) References Cited

U.S. PATENT DOCUMENTS 3,988,783 A  11/1976 Treace
4,246,660 A   1/1981 Wevers
(Continued)

FOREIGN PATENT DOCUMENTS

EP  2473135 A1  7/2012
GB  2126095 A   3/1984
WO  9103993 A1  4/1991

OTHER PUBLICATIONS

European Search Report for EP Application No. 18197888.3, dated Mar. 14, 2019.
(Continued)

*Primary Examiner* — Brian A Dukert
*Assistant Examiner* — Melissa A Hoban
(74) *Attorney, Agent, or Firm* — Lerner David LLP

(57) ABSTRACT

In one embodiment of the disclosure, a prosthetic bone implant includes a prosthesis and a tissue attachment structure connected to the prosthesis. The tissue attachment structure includes a connective structure connected to the prosthesis and an interface structure connected to the connective structure. The interface structure is configured for attachment of tissue thereto. When the interface structure is subject to tension, the connective structure changes in shape.

9 Claims, 6 Drawing Sheets

(51) Int. Cl.
*A61F 2/46* (2006.01)
*A61F 2/08* (2006.01)
*A61F 2/38* (2006.01)

(52) U.S. Cl.
CPC .............. *A61F 2/46* (2013.01); *A61F 2/3877* (2013.01); *A61F 2002/087* (2013.01); *A61F 2002/30011* (2013.01); *A61F 2002/30074* (2013.01); *A61F 2002/30164* (2013.01); *A61F 2002/30329* (2013.01); *A61F 2002/30565* (2013.01); *A61F 2002/30571* (2013.01); *A61F 2002/30579* (2013.01); *A61F 2002/30733* (2013.01); *A61F 2002/30985* (2013.01)

(56) References Cited

U.S. PATENT DOCUMENTS

| | | | |
|---|---|---|---|
| 5,163,961 A * | 11/1992 | Harwin | A61F 2/30739 |
| | | | 623/22.46 |
| 5,509,933 A * | 4/1996 | Davidson | A61B 17/72 |
| | | | 606/280 |
| 5,556,428 A * | 9/1996 | Shah | A61B 17/1146 |
| | | | 606/151 |
| 6,036,716 A * | 3/2000 | Kruchinin | A61B 17/0057 |
| | | | 604/104 |
| 6,371,985 B1 | 4/2002 | Goldberg | |
| 6,398,812 B1 | 6/2002 | Masini | |
| 6,592,622 B1 | 7/2003 | Ferguson | |
| 7,537,664 B2 | 5/2009 | O'Neill et al. | |
| 8,636,800 B2 | 1/2014 | Ferko et al. | |
| 8,728,387 B2 | 5/2014 | Jones et al. | |
| 9,135,374 B2 | 9/2015 | Jones et al. | |
| 9,180,010 B2 | 11/2015 | Dong et al. | |
| 9,456,901 B2 | 10/2016 | Jones et al. | |
| 9,833,326 B2 | 12/2017 | Porter et al. | |
| 2003/0014112 A1 * | 1/2003 | Ralph | A61F 2/442 |
| | | | 623/17.13 |
| 2004/0172138 A1 * | 9/2004 | May | A61F 2/3601 |
| | | | 623/20.36 |
| 2005/0229323 A1 * | 10/2005 | Mills | A61F 2/08 |
| | | | 8/94.11 |
| 2005/0251260 A1 * | 11/2005 | Gerber | A61F 2/4425 |
| | | | 623/17.13 |
| 2008/0021554 A1 | 1/2008 | Stone et al. | |
| 2011/0106265 A1 * | 5/2011 | Wolfson | A61F 2/0811 |
| | | | 623/18.11 |
| 2011/0130840 A1 | 6/2011 | Oskouei | |
| 2016/0199171 A1 * | 7/2016 | Dodd | A61F 2/3836 |
| | | | 623/13.14 |

OTHER PUBLICATIONS

Lee et al., U.S. Appl. No. 62/517,456, filed Jun. 9, 2017, titled "Polymer Interlock Support Structure and Method of Manufacture Thereof".

Stamp et al., U.S. Appl. No. 62/520,221, filed Jun. 15, 2017, titled "Porous Structures Produced by Additive Layer Manufacturing".

https://web.archive.org/web/20160808084450/http://smartstructures.wikispaces.com:80/Auxetic+Materials, Retrieved Aug. 8, 2016, 5 pages.

* cited by examiner

INTEGRATED SPRING FOR SOFT TISSUE ATTACHMENT

CROSS-REFERENCE TO RELATED APPLICATIONS

The present application claims the benefit of U.S. Provisional Patent Application No. 62/567,329, filed on Oct. 3, 2017, the disclosure of which is incorporated by reference herein in its entirety.

BACKGROUND OF THE INVENTION

The present invention relates to orthopedic implants that include attachments for soft tissues.

In certain surgical procedures, resection of a bone and replacement of the resected section with a prosthetic implant involves an additional step of reattaching critical soft tissues, such as ligaments of a joint. For instance, these circumstances may arise with replacement of one of a proximal end of the tibia near the knee, a proximal end of the humerus near the shoulder, or a proximal end of the femur near the hip, to name but a few examples.

In procedures where the soft tissue is reattached to the prosthesis, techniques that have been developed to obtain such reattachment often involve rigid fixation of the soft tissue to the prosthesis. For example, soft tissue may be sutured directly to a surface of the prosthesis, or to a porous surface on the prosthesis. Porous surfaces that have been used to perform this technique include porous coatings or foam rigidly fixed onto the prosthesis. However, this can result in a situation in which the interface between the soft tissue and the prosthesis must withstand shear forces generated when the soft tissue is subject to tension, which can lead to the soft tissue detaching from the prosthesis due to repeated cycles of loading over an extended period of time. Such risk is not mitigated merely by avoiding strenuous activity. In reconstructions involving attachment of the patellar tendon to a prosthesis, mere repeated bending of the knee may lead to excessive wear causing failure.

Thus, there is a need for improved prostheses for connection to soft tissue at joints within the body, as well as methods associated with same.

BRIEF SUMMARY OF THE INVENTION

Embodiments of the present invention solve the above described problem by providing a prosthetic bone implant with a tissue attachment structure that functions as an intermediate element between soft tissue to be connected to the prosthesis and the prosthesis itself. The tissue attachment structure includes a porous outer membrane and a connective structure such as a spring and is attached to the prosthesis in a matter so that the tissue attachment structure moves relative to the prosthesis as a function of tension in the attached soft tissue. Specifically, when the soft tissue is subject to tension, the connective structure changes in shape, absorbing load in the soft tissue so that a stress transferred to an interface with the prosthesis itself is lower than a stress in the soft tissue. Put another way, the tissue attachment structure acts as a shock absorber.

The prosthetic bone implant and any number of its constituent parts can be applied as a structure, kit or method in many joints within the body, such as at a proximal end of the tibia below the knee, a proximal end of the femur below the hip, or at a proximal end of the humerus near the shoulder, among others.

In one aspect, the present invention relates to a prosthetic bone implant. In one embodiment, the prosthetic bone implant includes a prosthesis and a tissue attachment structure with a connective structure and an interface structure. The tissue attachment structure is connected to the prosthesis through the connective structure. The interface structure is connected to the connective structure and is configured for attachment of tissue thereto. When the interface structure is subject to tension, the connective structure changes in shape.

In another embodiment, the prosthesis includes a first surface and a second surface recessed relative to the first surface. The prosthetic bone implant is positioned relative to the prosthesis so that the connective structure is attached to the prosthesis below the first surface. In a variant, the connective structure includes a first end and a second end, the first end attached to a first wall separating the second surface from the first surface and the second end attached to a second wall separating the second surface from the first surface. In yet another variant, the interface structure is connected to the connective structure on a side of the connective structure furthest from the second surface of the prosthesis.

In other embodiments, the tissue attachment structure is configured to move relative to the prosthesis when the interface structure is subject to tension. In a variant, the tissue attachment structure returns to its original position relative to the prosthesis when the tension applied to the interface structure is removed. In yet another embodiment, the at least one connective structure is a coil spring, a directional leaf spring, or an auxetic structure with a polyhedron shape. In still another embodiment, at least one of the prosthesis and the tissue attachment structure is made of a titanium alloy.

In another aspect, the present invention relates to a tissue attachment structure. In one embodiment, the tissue attachment structure includes a porous material layer and a connective structure. The porous material layer is configured for attachment to tissue. The connective structure includes a first location and a second location on its length such that it is connected to the porous material layer at the first location and the prosthesis at the second location. The connective structure is a spring or an auxetic structure.

In another embodiment, the tissue attachment structure also includes a lower material layer connected to the porous material layer with a lower porosity than the porous material layer. In a variant, the lower material layer is disposed in between the porous material layer and the connective structure.

In one embodiment, the connective structure is configured such that the connection of the connective structure to the porous material layer at the first location is in between two ends of the connective structure. The connective structure is configured for securement to the prosthesis at each of the two ends. In another embodiment, the connective structure is a directional leaf spring or a coil spring. In yet another embodiment, the connective structure has a Poisson's ratio between 0.28 and 0.50.

In one embodiment, the connective structure is an auxetic structure having a negative Poisson's ratio. In a variant, the auxetic structure has a polyhedron shape. In another embodiment, the porous material layer is a foam. In some embodiments, the connective structure, the lower material layer and the porous material layer are monolithic. In other embodiments, a method of manufacturing the tissue attachment structure involves using an additive manufacturing technique. In yet another embodiment, the tissue attachment structure and a prosthesis are combined to form a prosthetic bone implant.

In yet another aspect, the present invention relates to a tissue attachment structure with a first material layer, a second material layer and at least one connective structure. In one embodiment, the first material layer is configured for attachment to tissue and the second material layer is connected to the first material layer, where the second material layer has a lower porosity than the first material layer. The at least one connective structure is connected to the second material layer so that the second material layer is in between the connective structure and the first material layer and is adapted to change in shape when subject to tension. The tissue attachment structure is configured so that the connection between the at least one connective structure and the second material layer is at a first location on the connective structure and the at least one connective structure is configured to be connected to a prosthesis at a second location on the connective structure. When the at least one connective structure is connected to the prosthesis, a distance between the first location and the second location changes when at least one of the first and second material layers is subject to tension.

In another embodiment, when the at least one connective structure is connected to the prosthesis and at least one of the first and second material layers is subject to tension, a distance between the second material layer and the prosthesis increases. In yet another embodiment, the first location on the at least one connective structure does not move with respect to the second material layer when one of the first and second material layers is subject to tension.

In another embodiment, the at least one connective structure is two connective structures, each connected to the second material layer at respective first locations on the connective structures and configured for connection to a prosthesis at respective second locations on the connective structures. In yet another embodiment, the at least one connective structure is a coil spring, a directional leaf spring, or an auxetic structure with a polyhedron shape. In one embodiment, the at least one connective structure, the second material layer and the first material layer are monolithic. In other embodiments, a method of manufacturing the tissue attachment structure involves using an additive manufacturing technique. In yet another embodiment, the tissue attachment structure and a prosthesis are combined to form a prosthetic bone implant.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

The present invention relates to apparatuses, kits and methods for preventing soft tissue attachments attached to a prosthesis from tearing off due to shear forces at an interface between the two. In one respect, tissue attachment structures as disclosed herein act as a shock absorber when soft tissue attached to the attachment structure is stressed. This mitigates the risk of the soft tissue detaching from the prosthesis.

Although many of the embodiments herein are described as directed to a prosthesis for a portion of the tibia below the knee including an attachment structure for attachment of the patellar tendon thereon, it is envisioned that the same embodiments can be employed in any area of the body where a prosthesis is implanted and connects to a ligament or other connective tissue. For example, the prosthetic bone implant may be implanted at a proximal end of the humerus below the shoulder with a connection to a capsular ligament at a natural location of the greater tuberosity. In another example, the prosthetic bone implant may be implanted at a proximal end of the femur below the hip with a connection to an upper portion of the iliofemoral ligament at a natural location of the greater trochanter. Prosthetic bone implants as described herein include, for example, bone replacement devices.

Figure 1:
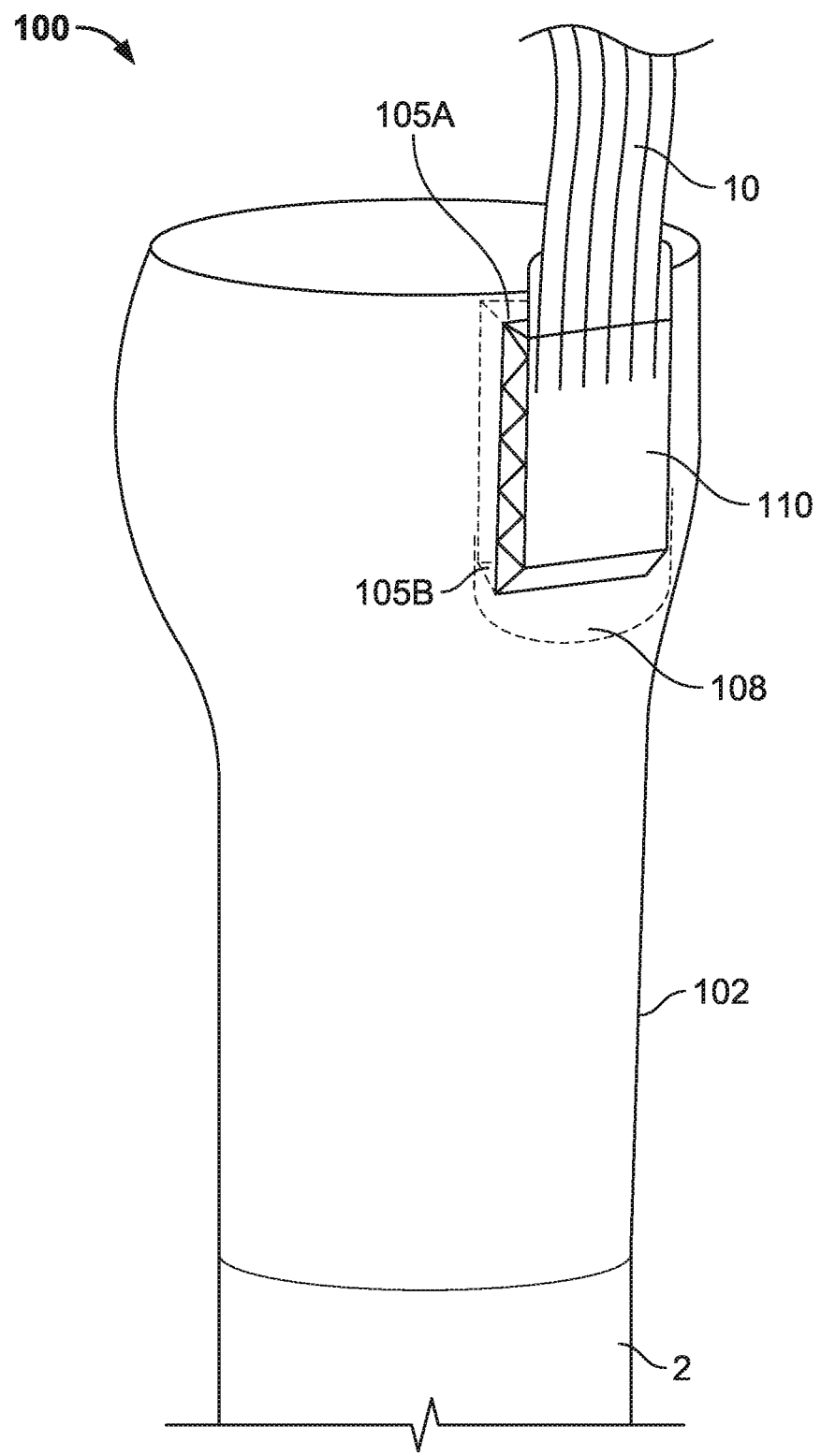
FIG. 1 is a perspective view of a prosthetic bone implant according to one embodiment of the present invention.
Figure 2:
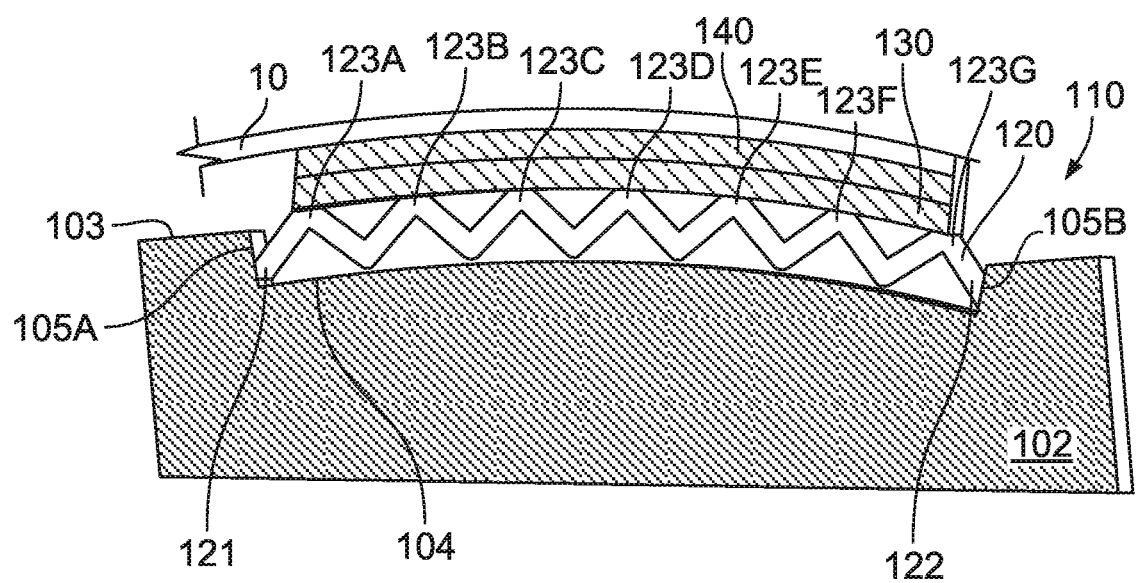
FIG. 2 is a partial sectional view of the prosthetic bone implant of FIG. 1.
Figure 3:
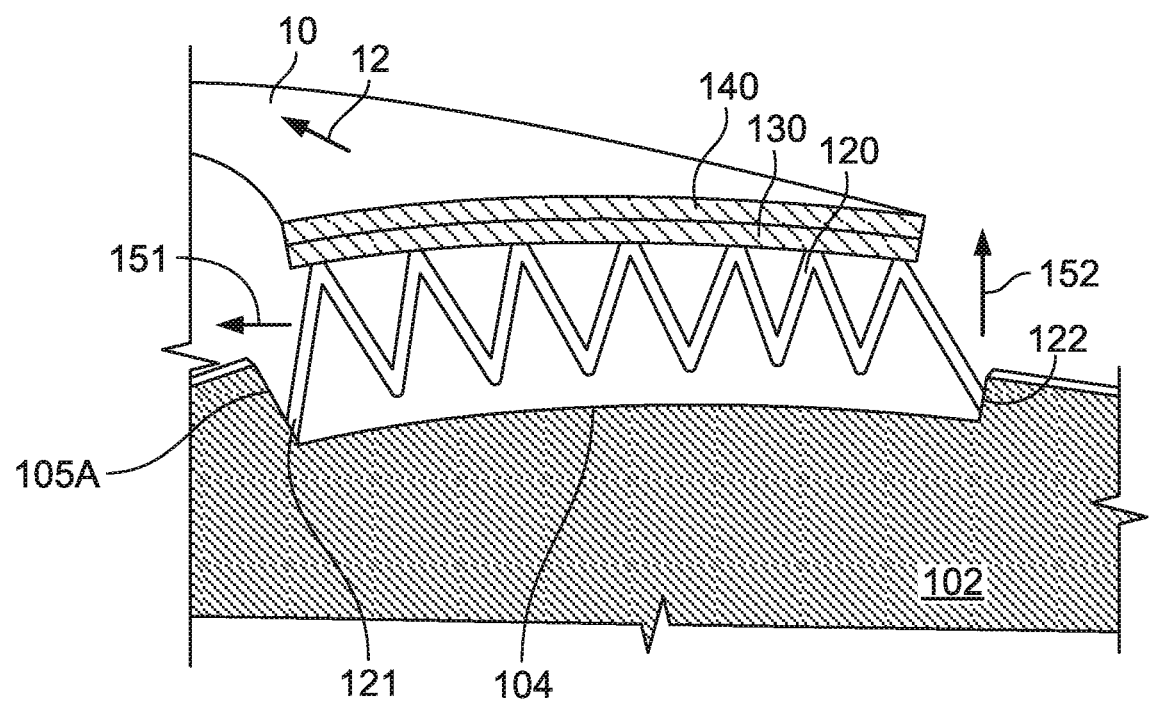
FIG. 3 is a partial sectional view of the prosthetic bone implant shown in FIG. 2 when attached tissue is subject to tension.

In one aspect, the present invention relates to a prosthetic bone implant. In one embodiment, a prosthetic bone implant 100 replaces a proximal end of tibia 2, as shown in FIG. 1. Bone implant 100 includes a tibial prosthesis 102 and a tissue attachment structure 110 located proximal to a natural location of tibial tubercle 108. In a fully implanted state, soft tissue is attached to tissue attachment structure 110 to form a connection between such tissue and the prosthesis. This is shown in FIG. 1 through attachment of patellar tendon 10 to tissue attachment structure 110, which in turn is connected to tibial prosthesis 102. Tissue attachment structure 110 has several constituent parts, as depicted in FIGS. 2 and 3. These include a connective structure in the form of a coil spring 120, a solid material layer 130, and an interface structure in the form of a porous material layer 140. In one variant, porous material layer 140 is a foam. As shown in FIGS. 2 and 3, coil spring 120 is the lowest layer in structure 110 and is directly connected to prosthesis 102. Solid material layer 130 is directly connected to spring 110, while porous material layer 140 is directly connected to solid material layer 130.

Tibial prosthesis 102 is sized, shaped, and otherwise designed to meet necessary requirements for implantation in a body of a patient. As depicted, tibial prosthesis 102 includes an exterior surface 103 and a recessed surface 104. Separating each of these surfaces are walls 105A, B, and walls between those walls (not shown in FIG. 2). Connection of tissue attachment structure 110 to tibial prosthesis 102 on walls 105A, B allows solid material layer 130 and porous material layer 140 to remain closer to exterior surface 103 and therefore cause less obstruction to other bodily tissue away from exterior surface 103 of prosthesis 102 than would otherwise occur with a tissue attachment structure placed over exterior surface 103. This is visible in FIG. 2, where it can be seen that porous material layer 140 would be further from exterior surface 103 if spring 120 were directly connected to exterior surface 103.

As shown in FIGS. 2 and 3, a single coil spring 120 is included as part of tissue attachment structure 110. In variants, however, two or more coil springs 120 may be included. Coil spring 120 is connected to tibial prosthesis 102 at ends 121, 122. The connection at ends 121, 122 is configured so that ends 121, 122 do not move relative to a corresponding location on walls 105A, 105B, respectively. A secure connection between the spring and the prosthesis is provided by connection mechanisms typically used to secure coil springs to another object. For example, a retainer structure (not shown), may be used. The retainer structure is disc shaped and includes a groove on an outer face at its circumferential perimeter so that an end section of the coil may be disposed within the groove. A bolt or other fastener holds the retainer in place relative to the prosthesis. Other mechanisms to connect the spring to the prosthesis are also contemplated, such as use of a sleeve that slides over and around the end of the coil and is fastened to the prosthesis using a metal adhesive, for example. In any of the aforementioned connection types, and in others, securement via welding is also contemplated. In yet another example, the tissue attachment structure and prosthesis are monolithic and are formed layer-by-layer using an additive layer manufacturing (ALM), i.e., 3D printing, process so no separate connection mechanism is necessary to bring together any of the components of the prosthetic bone implant. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein. Assembly of a prosthetic bone implant in whole or in part using ALM is discussed in greater detail below. It should be appreciated that these connection mechanisms are merely exemplary and are not limiting in any way. In this manner, other connection mechanisms may also be included as part of the prosthetic bone implant as deemed appropriate. In addition to its connection to prosthesis 102, coil spring 120 is connected to solid material layer 130 at locations 123A-G, described in greater detail below.

Structurally, coil spring 120 is configured to have a helical radius and a shear modulus to accommodate a range of movement of the coil spring that corresponds to a potential range of movement of porous and solid material layers 130, 140 relative to prosthesis 102. Specifically, coil spring 120 is configured so that a first portion compresses while a second portion expands when patellar tendon 10, i.e., soft tissue, is subject to tension, such as tension depicted by arrow 12 in FIG. 3. When attached tissue is in tension, as shown in FIG. 3, the compressed portion of spring 120 is closest to end 121 while the tensioned portion is closest to connection 122. Compression and expansion of coil spring 120 are relative to an at rest shape of coil spring 120, extant in the absence of loading.

Solid material layer 130 is a membrane positioned in between coil spring 120 and porous material layer 140, as shown in FIG. 2. Solid material layer 130 is connected to coil spring 120 at each location 123A-G on spring 120, as shown in FIG. 2. In variants, any number or combination of locations 123A-G may be connection points between the solid material layer and the coil spring. The connection mechanism between coil spring 120 and solid material layer 130 may be any known to those of ordinary skill in the art, such as those described above. Because space is limited at an interface between solid material layer 130 and spring 120, a weld or series of welds is typically used where additive manufacturing is not employed. Alternatively, an adhesive suitable for the adjoining materials may also be used. This structural arrangement, as shown in FIGS. 2 and 3, provides a non-rigid connection of porous and solid material layers 130, 140 with prosthesis 102 via coil spring 120. The connection is not rigid because the porous and solid material layers 130, 140 are moveable with respect to prosthesis 102.

Solid material layer 130 is composed of materials with sufficient elasticity so that integrity of the solid material layer is maintained under repeated expansion and contraction of coil spring 120. A particular thickness and width of solid material layer are a matter of design choice, although the structural properties based on the materials and dimensions used should be sufficient to withstand expected loads from tension forces in attached patellar tendon 10. In this manner, no tearing or other failure of solid material layer 130 should occur when the joint, here, the knee, operates under an expected range of motion.

As shown in FIG. 2, porous material layer 140 is fixed relative to solid material layer 130 via an adhesive or other securement element as known to those of ordinary skill in the art. A particular type of connection between these elements may be chosen as a function of the materials used for porous material layer 140 and solid material layer 130, respectively. In some examples, the porous material layer and solid material layer are formed using an ALM process, such as those described above, and no additional securement element is required. The geometry of the porous material layer is shaped to mimic the anatomy at the relevant placement location over the prosthesis that replaces a portion of a bone structure. Porous material layer 140 is porous, particularly relative to solid material layer 130. The porosity of porous material layer 140 is sufficient to promote tissue ingrowth over time when tissue is attached thereon, as well as to aid in the initial fixation prior to ingrowth occurring. For instance, porous material layer 140 is configured so that tissue may be temporarily secured thereto with sutures or other similar connective elements while the tissue grows into the porous layer.

Each of prosthesis 102, coil spring 120, solid material layer 130, and porous material layer 140 may be constructed of a titanium alloy, another metal, or a flexible material. Flexible materials that may be used include Dacron, polytetra fluoroethylene, texturized or open-weave poly(ethylene terephthalate), waterswolen poly(2-hydroxyethyl methacrylate), polydioxanone, PDO/Elastin weave, polyurethane, aromatic porous polyurethane, poly-(L-lactic acid), Polyetheretherketone, allograft or xenograft tendon or ligament, small-intestinal submucosa, collagen, cell seeded collagen matrices, hydrogels, and Chitosan. In some variants, modified titanium alloy or other metals may be used that possess greater flexibility than standard compositions of the respective metal. All constituent parts of prosthetic bone implant 100 may be a common material, such as one of those listed above, or different materials can be employed for each part. Particular combinations of materials and their use for specific parts of the prosthetic bone implant are a matter of design choice. Further, although specific materials are described above, it is contemplated that other materials may also be used for the constituent parts of prosthetic bone implant 100 as a matter of design choice. In some variants, a material chosen for the spring has a poisson's ratio between 0.28 and 0.50. Many varieties of steel, titanium and polymers have a poisson's ratio within this range.

Figure 4:
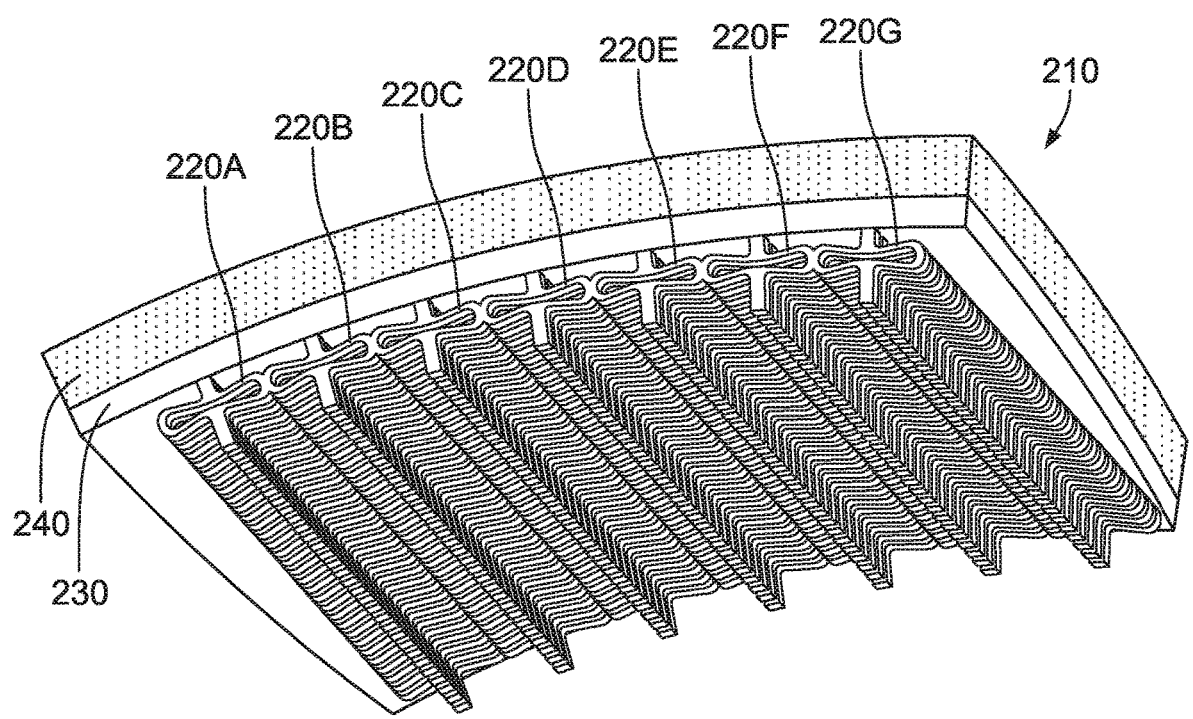
FIG. 4 is a perspective view of a tissue attachment structure according to one embodiment of the present invention.

In another embodiment, a prosthetic bone implant includes a tissue attachment structure 210 as shown in FIG. 4. Unless otherwise stated, like reference numerals refer to like elements, but within the 200-series of numbers. In tissue attachment structure 210, multiple springs 220A-G are used to provide for movement of porous and solid material layers 240, 230 relative to a prosthesis (not shown). These springs 220A-G are oriented perpendicular to a lower surface of solid material layer 230 above the springs. Each spring includes a lower and upper vertical arm with a pair of laterally extending loops in between. Springs 220A-G are configured to expand and contract through expansion and contraction of the laterally extending loops. The characteristics of the loops ensure that each spring 220A-G absorbs loads from tension in a soft tissue attached to tissue attachment structure 210. The lower vertical arm of each spring 220A-G serves as a connection point to secure tissue attachment structure 210 to the prosthesis. One example of securement includes welding. In another example, no separate securement is necessary because tissue attachment structure 210 is formed using an ALM process.

Figure 5:
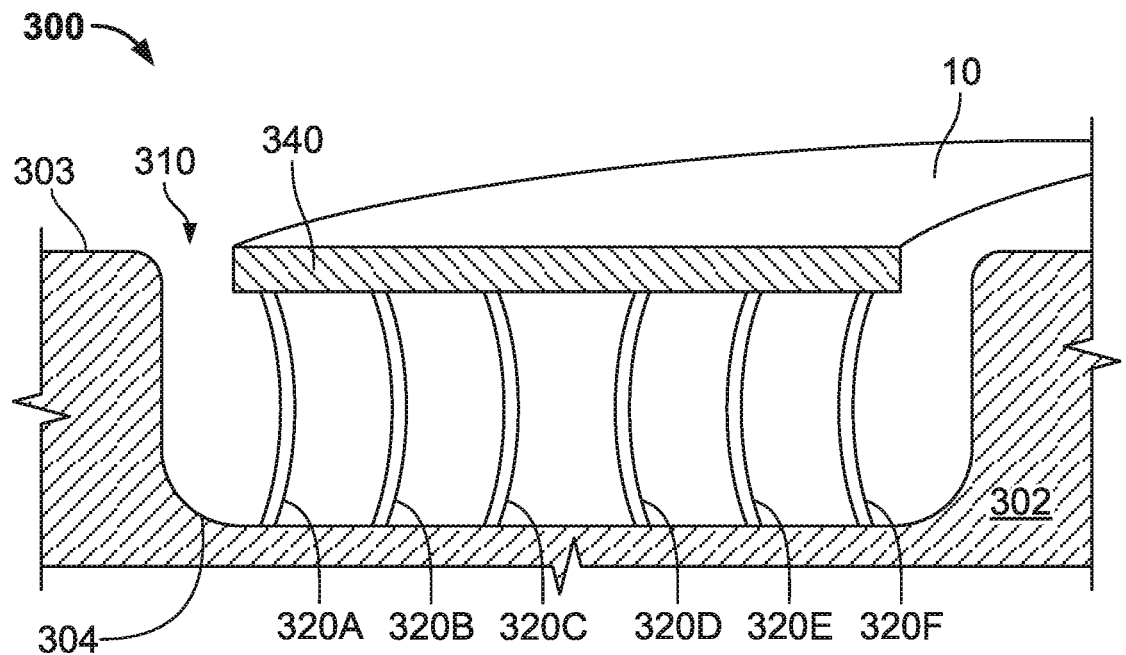
FIG. 5 is a partial sectional view of a prosthetic bone implant according to one embodiment of the present invention.
Figure 6:
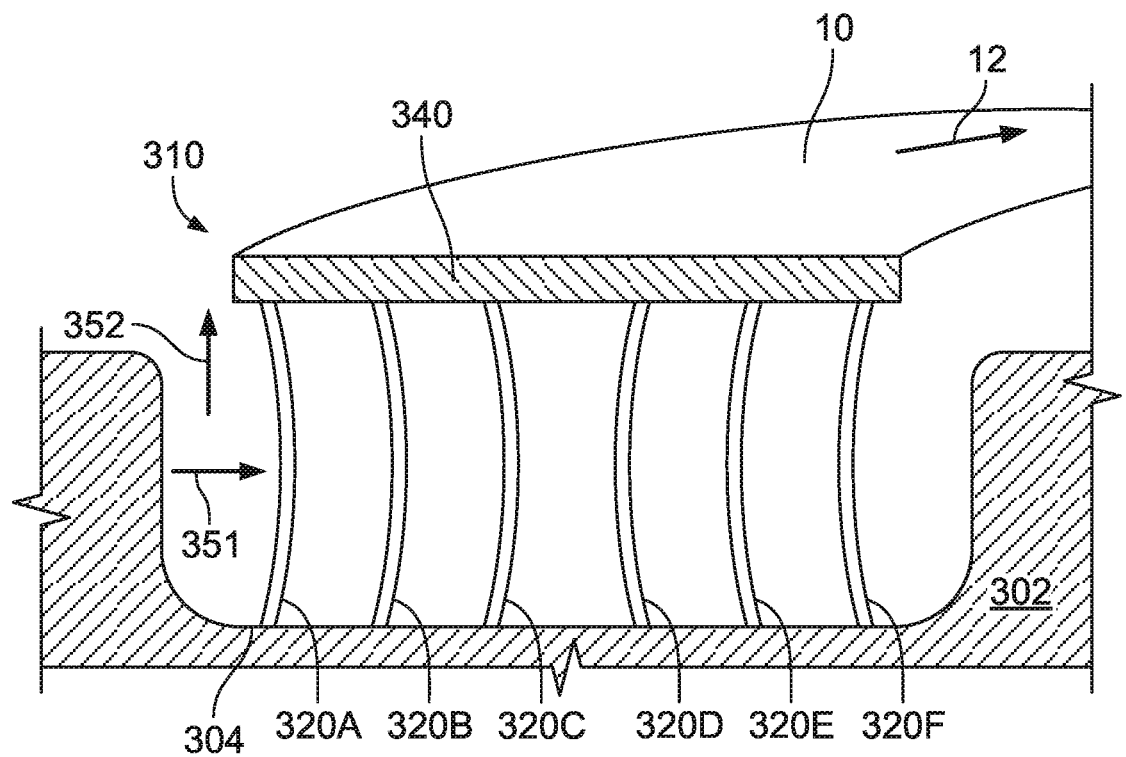
FIG. 6 is a partial sectional view of the prosthetic bone implant shown in FIG. 5 when attached tissue is subject to tension.

Another embodiment of a prosthetic bone implant 300 with a prosthesis 302 and tissue attachment structure 310 is shown in section in FIGS. 5 and 6. Again, unless otherwise stated, like reference numerals refer to like elements, but within the 300-series of numbers. Tissue attachment structure 310 includes a porous material layer 340 and directional leaf springs 320A-F. Directional leaf springs 320A-320F are included as part of the tissue attachment structure to allow porous material layer 340 to move relative to prosthesis 302. As with the springs in tissue attachment structures 110, 210, the leaf springs absorb stresses in attached soft tissue. Each spring 320A-F is connected to porous material layer 340 at one end and to a lower surface 304 within a recess of prosthesis 302 at another end. Securement elements to secure leaf springs 320A-F may be those typically used to secure leaf springs as would be known to those of skill in the art. For example, leaf springs may have one or more coiled ends (not shown) so that an anchoring element can be disposed through such coil and secured to the prosthesis via welding or another technique. The anchoring element in such cases can be a U-bar, hook, or other structure. In other examples, adhesives may be used. Adhesives or other minimally invasive connection mechanisms are most likely to be employed at the interface of the coil spring and the porous material layer. In still further examples, the entire prosthetic bone implant is monolithic, e.g., manufactured using ALM, and no separate securement elements are necessary. In FIGS. 5 and 6, the springs as shown are single leaf springs, although it is contemplated that multiple leaf springs may also be used.

As with the other embodiments described herein, each spring 320A-F is configured to be at rest when porous material layer 340 is not subject to loading. In the at rest position, springs 320A-C are curved so that a midpoint of each is closer to a center of tissue attachment structure 310 than the ends while springs 320D-320F are also curved so that a midpoint of each is closer to the center, as shown in FIG. 5. In this manner, springs 320A-C mirror springs 320D-F. Springs 320A-F are configured so that under loading, a curvature of each spring changes in response to tension in the connected tissue 10. Although bending of each spring along its length is the primary mode of deformation, the springs are also configured to extend in length due to loads pulling away from the springs, at least nominally. In some variants, the position of each spring relative to the soft tissue and the other springs varies from that depicted in FIGS. 5 and 6.

Figure 7:
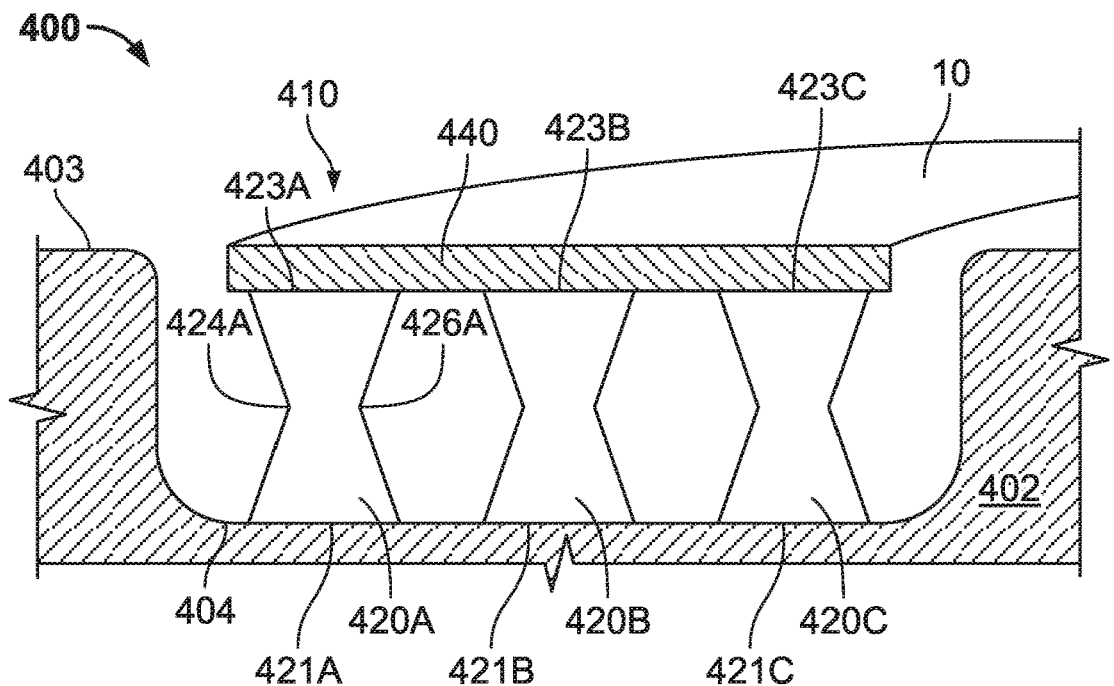
FIG. 7 is a partial sectional view of a prosthetic bone implant according to one embodiment of the present invention.
Figure 8:
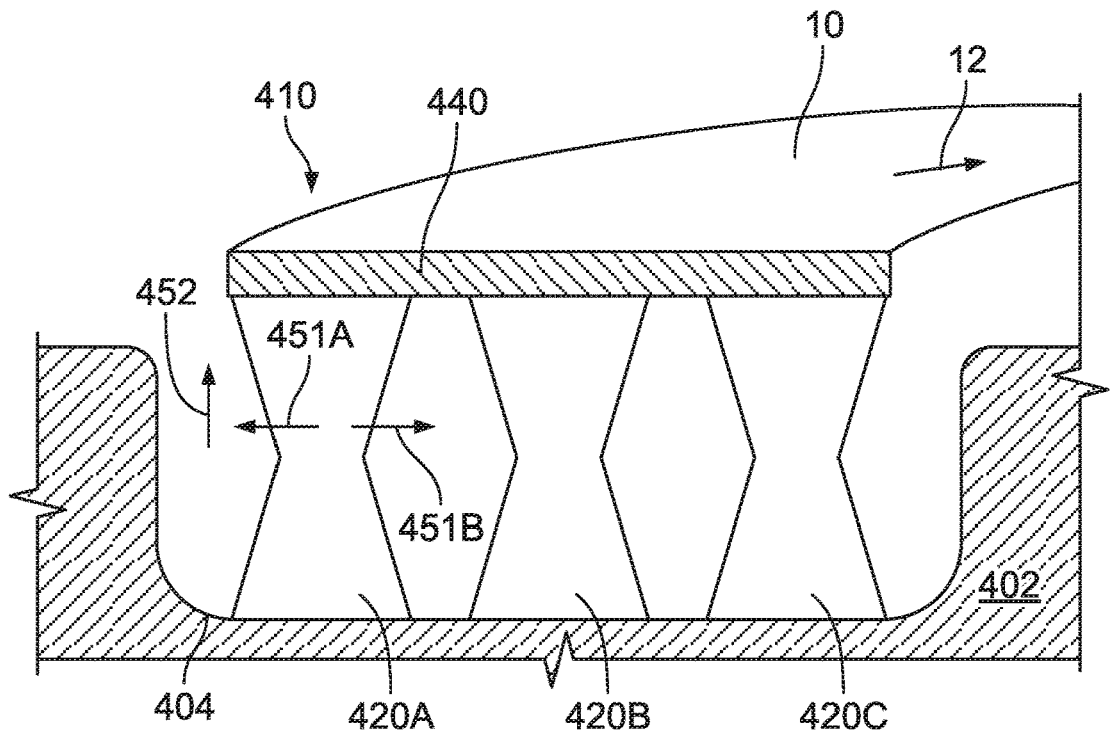
FIG. 8 is a partial sectional view of the prosthetic bone implant shown in FIG. 7 when attached tissue is subject to tension.

Yet another embodiment of a prosthetic bone implant 400 is shown in section in FIGS. 7 and 8. Unless otherwise stated, like reference numerals refer to like elements, but within the 400-series of numbers. Tissue attachment structure 410 of implant 400 includes a porous material layer 440 and auxetic hexagon structures 420A-C. As with the springs described above, auxetic hexagon structures 420A-C allow porous material layer 440 to move relative to prosthesis 402 so that the porous material layer remains attached to the prosthesis even when subject to cyclic loading. Incorporation of auxetic structures such as the auxetic hexagon elements into the tissue attachment structure have additional advantages in that they provide increased shear stiffness, increased fracture toughness and increased indentation resistance when compared to non-auxetic materials. Each auxetic hexagon structure 420A-C is connected to porous material layer 440 at one end 423A-C and to a lower surface 404 within a recess of prosthesis 402 at another end 421A-C. Connection is achieved through securement elements as known in the art, such as welds and structural adhesives. A choice of securement type may be guided by the material of both the auxetic hexagon structure and the prosthesis. No separate securement elements are included when prosthetic bone implant including prosthesis 402 and tissue attachment structure 410 are formed using an ALM process, as the combined structure is monolithic.

As their name suggests, auxetic hexagon structures are auxetic and possess a negative poisson's ratio. In practical terms, this means that as a length of each auxetic hexagon increases, its width also increases, unlike materials with a positive poisson's ratio, whose width will decrease in conjunction with length increase. Each auxetic hexagon structure has a neck defined by hinge points, such as points 424A, 426A for auxetic hexagon structure 420A, as shown in FIG. 7. Auxetic hexagon structures 420A-C are configured so that when tensioned, i.e., subject to forces drawing connection locations 421A, 423A further apart, hinge points 424A, 426A are caused to move laterally outward away from one another.

Figure 9:
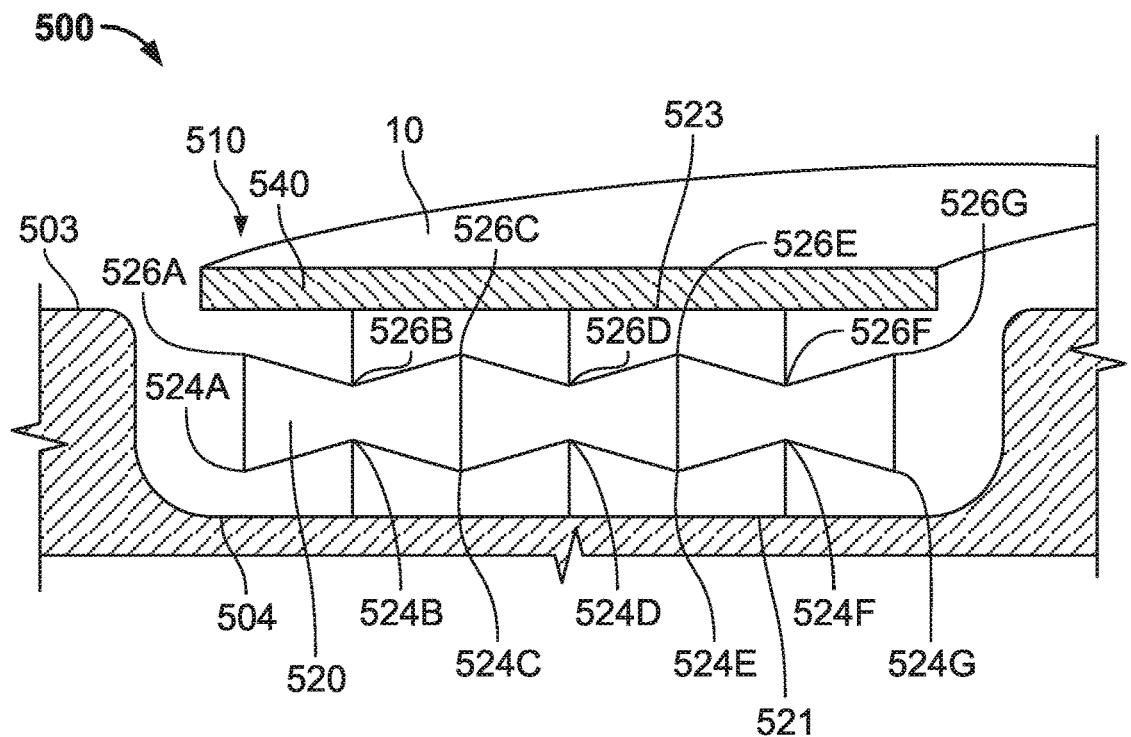
FIG. 9 is a partial sectional view of a prosthetic bone implant according to one embodiment of the present invention.
Figure 10:
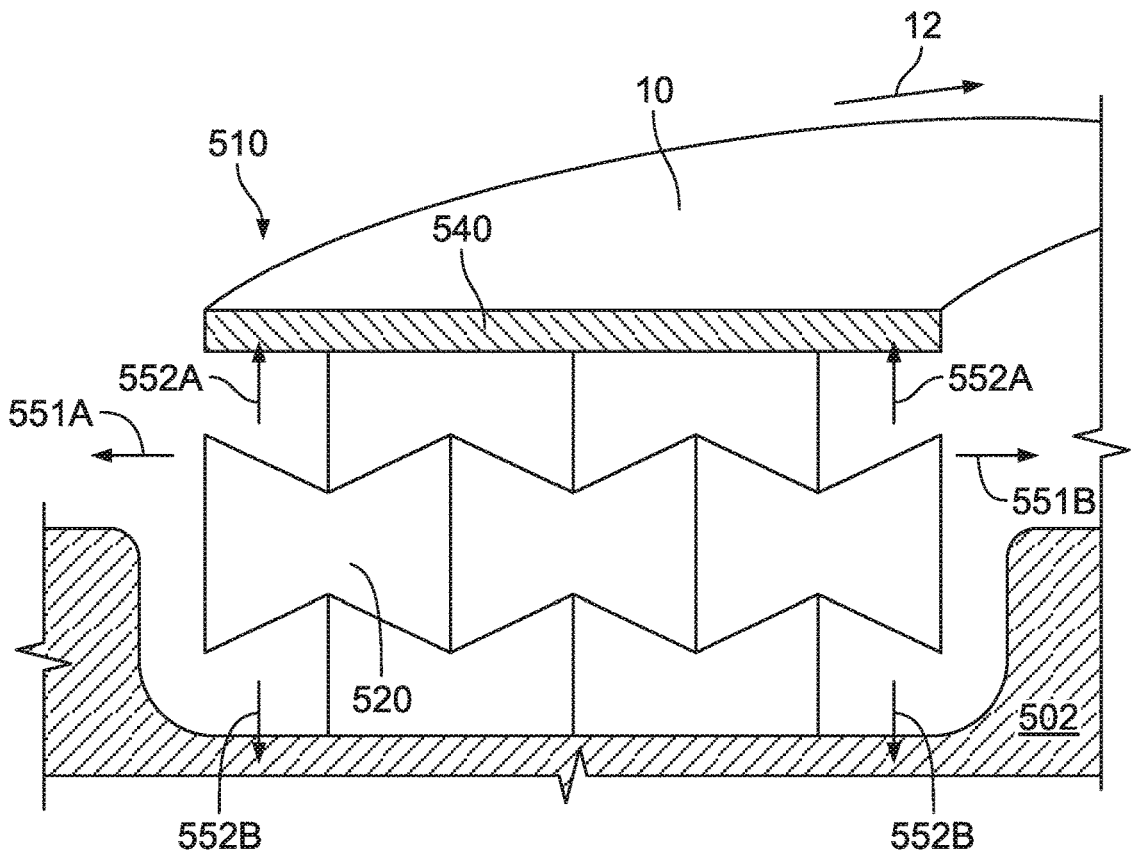
FIG. 10 is a partial sectional view of the prosthetic bone implant shown in FIG. 9 when attached tissue is subject to tension.

In yet another embodiment, a prosthetic bone implant 500 is as shown in section in FIGS. 9 and 10. Again, unless otherwise stated, like reference numerals refer to like elements, but within the 500-series of numbers. Tissue attachment structure 510 of implant 500 includes a porous material layer 540 and a single auxetic polyhedral structure 520. As with the springs and auxetic structure described above, auxetic polyhedral structure 520 connects porous material layer 540 to prosthesis 502 and allows porous material layer 540 to move relative to prosthesis 502 so that the porous material layer 540 remains attached to the prosthesis even when subject to cyclic loading. Auxetic polyhedral structure 520 is connected to porous material layer 540 at one end 523 and to a lower surface 504 within a recess of prosthesis 502 at another end 521. Securement elements may be as described for tissue attachment structure 410, for example. In other examples, tissue attachment structure 510 is formed using an ALM process.

As with auxetic hexagon structures 420A-C, auxetic polyhedral structure 520 has a negative poisson's ratio. Although not shown in its entirety in FIGS. 9 and 10, polyhedral structure 520 has twenty-four planar surfaces. Each surface, or face, has six sides, as shown in FIG. 9. For example, one surface is defined by outer hinges 524A, C, 526A, C and inner hinges 524B, 526B, the latter located in a neck region. Auxetic polyhedral structure 520 is configured so that when it is subject to tension, movement of outer hinges 524A, 524C away from one another is accompanied by movement of inner hinges 524B, 526B away from one another. This behavior is present on each face of the polyhedral structure. In this manner, auxetic polyhedral structure 520 expands both laterally and longitudinally in multiple planes.

The auxetic materials used for tissue attachment structures 410, 510 can be varied in many ways. For example, it is possible to produce auxetic materials from a wide variety of materials including polymers, composites, metals and ceramics. A Young's modulus, E, i.e., stiffness, for the materials can vary as a matter of design choice to suit a desired application. Specific examples of auxetic materials include auxetic polyurethane foam, auxetic graphene and certain variants of polytetrafluoroethylene polymers, such as Gore-Tex, among many others. A shape of auxetic materials can also vary in innumerable ways. For example, the auxetic structure can be a polyhedron with any number of planar faces. Such auxetic structures can be used when multiple structures are included, such as the arrangement shown in FIGS. 7-8, or when the auxetic structure is singular, such as the arrangement shown in FIGS. 9-10.

In some embodiments, a recessed volume of the prosthesis spans a surface area larger than that covered by the tissue attachment structure of the prosthetic bone implant. Such recessed volume may also vary in depth across the surface area. In other embodiments, the tissue attachment structure is disposed on the exterior surface of the prosthesis and is not disposed in a recessed volume defined by a recessed surface in the prosthesis at all. In such a structure, the prosthesis may have recessed portions, but such recesses are separate from the placement location of the tissue attachment structure. It is also contemplated for any of the embodiments disclosed herein that the materials constituting the prosthesis may be distinguishable from any constituent part of the tissue attachment structure.

In any one of the above embodiments, the number of connection locations between the springs or auxetic structures and the prosthesis may be one, two, three, or more. A distance and direction of each connection location relative to another on a surface of the prosthesis may be any value and is not a function of a distance between other pairs of connection locations. For example, a first spring and a second spring may be connected to a prosthesis adjacent to one another but their respective connections to a porous material layer may be at different locations on a length of each spring.

In other embodiments, the connective structure used for the tissue attachment structure may be conical coil springs or flat springs. In some cases, it may be desirable to use belleville disc springs, provided performance of the implant with uniaxial movement of the spring is sufficient. In other examples, the spring includes a series of flexible struts formed using an ALM process such as that described below and in U.S. Prov. Pat. App. No. 62/520,221, hereby incorporated by reference herein in its entirety. These springs can be any number of shapes and can have any amount resistance to tension in their at rest position as a matter of design choice. In any one of the embodiments described herein, the number of springs or auxetic structures forming part of a particular tissue attachment structure may be one, two, or more. In still further embodiments, the number of tissue attachment structures connected to a particular prosthesis may be two or more. For example, where the prosthesis replaces a proximal end of the femur at the hip, two tissue attachment structures may be connected to the prosthesis. One may be positioned at the natural location of the greater trochanter and connected to an upper segment of the iliofemoral ligament while another may be positioned at the natural location of the lesser trochanter and connected to a lower segment of the iliofemoral ligament, separate from the upper segment. In some embodiments, the material of the porous material layer and the connective structure, such as the spring or auxetic structure, vary with respect to one another. Where the tissue attachment structure includes a solid material layer, such material can also vary so that two, three, or more materials make up the tissue attachment structure.

In any one of the above embodiments, the porous material layer of the tissue attachment structure can include extensions in the form of an arm or arms with a slot as disclosed in commonly owned U.S. Pat. No. 8,636,800, hereby incorporated by reference herein in its entirety. Such an extension is of particular import where a soft tissue to be secured to the prosthesis is otherwise too short to connect directly to a tissue attachment structure immediately adjacent to the prosthesis surface. In any one of the above embodiments, the tissue attachment structure may include a porous material layer attached to a spring or auxetic structure with or without a solid material layer in between. In any one of the above embodiments, the tissue attachment structure may be prepared as the sole apparatus of the embodiment, without a prosthesis. In this manner, the tissue attachment structure may be stored and distributed for later use with a prosthetic as desired.

In another aspect, two or more of the above tissue attachment structures and prostheses may be included together as a kit. In one embodiment, a kit is contained in a single package as a system or in multiple packages that can be selected as needed by the operator to form a system. For example, such a kit may include one of each of two types of tissue attachment structures. Where the kit includes more than one tissue attachment structure, the plurality of tissue attachment structures can vary in overall size, spring or auxetic structure quantity, and materials, or the like, from which the most suitable elements may be chosen for a particular surgical procedure. In other examples, the kit may include one or more of a tissue attachment structure and associated prosthesis. Any combination of tissue attachment structures and prostheses may also be included in a single package or in separate packaging which are later brought together as a kit. In another example, the tissue attachment structures may be packaged separately due to their various sizes.

The kit may be varied in many ways. It is contemplated that any combination of the structures described herein and associated accessories may be included as part of a kit. For example, the kit of the above embodiments may also include tools for creating an incision, tools for placing the implant components, sutures, and other accessories that accompany surgeries contemplated by the embodiments of the present invention. Such elements can be included as single elements or more than one may be included. The various combinations of elements of any contemplated kit may be included in a single package or distributed among multiple packages. In other examples, the kits contemplated herein may be accompanied by an instruction manual on how to perform one or more of the methods of using the contents within the applicable kit.

In another aspect, the present invention relates to methods of using a prosthesis adjacent to a joint that includes a tissue attachment structure so that soft tissue, e.g., a ligament, may function in conjunction with the prosthesis. In specific applications, a tissue attachment structure on the prosthesis is positioned in the body of the patient at a natural location of one of a tibial tubercle, greater trochanter, or a humeral tuberosity, to name but a few examples, to act as a shock absorber to mitigate the possibility that a soft tissue attachment may shear off an associated prosthesis.

In one embodiment, as shown in FIG. 1, a tibial prosthesis 102 is initially in place on a tibia and includes a tissue attachment structure 110 connected to its surface. In preparation for use of the prosthesis, tissue attachment structure 110 is connected to or formed with prosthesis 102 immediately above a location of the tibial tubercle 108 so it can mimic the natural location for attachment of the patellar tendon. Patellar tendon 10 is then connected to porous material layer 140 using sutures or other similar connective elements. The combination of the porous material and the tissue is such that, over time, tissue grows in to the porous layer. When sufficient recovery time has lapsed, the knee of the treated patient will be ready to withstand bending.

In a first step, the knee is bent so that patellar tendon 10 goes into tension and pulls away from prosthesis 102, as shown in FIG. 3. Because spring 120 is located in between tendon 10 and prosthesis 102, spring 120 absorbs the force in the tendon 10 and transfers it to the prosthesis through ends 121, 122 connected to prosthesis 102. This minimizes any shear force at the interface of the tendon 10 and prosthesis 102 that would otherwise exist, which could cause failure of the tissue attachment. Characterizing this process in greater detail, when tendon 10 goes into tension, as depicted by arrow 12 and shown in FIG. 3, spring 120 compresses proximal to the knee joint at end 121 and expands over a portion near end 122. Concurrent with these changes in the shape of spring 120, connection points 123A-G move with tendon 10 in a direction shown as arrow 151 corresponding to a horizontal component of the tension force in tendon 10. Since interfaces between solid material layer 140 and spring 120 allow the spring to move with tendon 10 under minimal resistance, the difficulties surrounding a fixed interface are minimized if not eliminated. Connection points 123A-G may also move away from surface 104 of prosthesis 102 in a direction shown by arrow 152 to the extent the tension in tendon 10 also extends away from surface 103 of prosthesis 102.

When the leg of the patient is straightened again, tension in tendon 10 abates and returns to its initial level. Spring 120 correspondingly reverts to its natural shape as shown in FIG. 2. Because spring 120 is elastic, bending and straightening of the leg with the prosthesis implanted therein may be repeated many times over a long period without fear of imminent detachment of the patellar tendon from the tibia. One reason for this improvement is because the motion of the knee is performed without subjecting the connection between the tissue and the prosthesis to excessive shear forces.

The above method may be varied in many ways. For example, tissue engagement structures as shown in FIGS. 4-10 may be used in place of those shown in FIGS. 1-3. Steps in preparation and use of the implant are essentially the same for these alternative structures, although movement of the tissue engagement structure relative to the prosthesis and the transfer of forces between the two varies to an extent.

For tissue attachment structure 210 of FIG. 4, when a tissue (not shown) connected to porous material layer 240 is tensioned, springs 220A-G expand with movement of the tissue, thus absorbing a measurable amount of resistance in the form of shear force that would otherwise exist at the interface of the tissue and the prosthesis. Tissue attachment structure 310 shown in FIGS. 5 and 6 operates in a similar manner. FIG. 6 shows leaf springs 320A-F bending and otherwise changing in shape in response to tension forces 351, 352 in tissue 10 due to bending of the joint.

Both tissue attachment structure 410 shown in FIGS. 7-8 and tissue attachment structure 510 shown in FIGS. 9-10 include auxetic structures that deform when subject to tension. In both cases, a method of use involving rotation of a tibia about a knee (in keeping with the embodiments described above), causes patellar tendon 10 to go into tension, e.g., as depicted by arrow 12, pulling on the auxetic structures via porous material layers 440, 540, respectively. With tissue attachment structure 410, each auxetic hexagon structure 420A-C expands laterally outward as shown, for example, by arrows 451A-B at hinge locations 424A, 426A and also outward in direction shown by arrow 452. In this manner, each auxetic hexagon structure 420A-C expands in size longitudinally and laterally. Similarly, with tissue attachment structure 510, auxetic structure 520 expands, both longitudinally as depicted by arrows 551A-B and laterally, or orthogonal to prosthesis 502 surface, as depicted by arrows 552A-B, when tendon 10 is subject to tension. In both tissue attachment structures 410, 510, stress in tendon 10 is transferred to prosthesis 402, 502 through recessed surface 404, 504 in the prosthesis, although the force in the tendon is significantly absorbed through the deformation of the auxetic structures prior to reaching the prosthesis.

The method of using the prosthetic implant structure can be varied in many ways. For example, the method can begin at any step described above and continue through the remaining steps. In another example, the method can begin as described above and end prior to completing each of the above steps. As noted above, the methods described herein can be performed in many different joints of the body, such as the shoulder and the hip.

In yet another aspect, the present invention relates to a method of assembling a prosthetic bone implant. In one embodiment, welds, an adhesive, or another securement element is used to bring together the spring of the tissue attachment structure and the prosthesis. The tissue attachment structure is connected to the prosthesis either before or after implantation of the prosthesis in the surgical site. Once prosthesis 102 with tissue attachment structure 110 secured thereon is safely implanted in the patient, patellar tendon 10 is secured to porous material layer 140 of tissue attachment structure 110 using sutures or other similar means. In other embodiments, such as those shown in FIGS. 4-10, similar techniques are used to assemble the prosthetic bone implant.

In some arrangements, the prosthetic bone implant is formed using an ALM fabrication process, such as SLS, SLM or EBM described above, fused deposition modeling (FDM), or other appropriate 3D printing technologies known to those skilled in the art. When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the prosthesis, the connective structure, the porous material layer, and any other components, as applicable. In some instances, materials for one layer may be different than the materials for successive layers.

To form the porous layer in particular, porous geometries may be digitally modeled using cells as described in U.S. Pat. Nos. 9,180,010 and 9,135,374, the disclosures of which are hereby incorporated by reference in their entireties herein. A first layer or portion of a layer of powder is deposited and then scanned with a high energy beam to create a portion of a plurality of predetermined porous geometries. Successive layers of powder are then deposited onto previous layers of the powder and then scanned with the high energy beam. The scanning and depositing of successive layers of the powder continues the building process of the predetermined porous geometries. The porous geometries of the formed porous layers may define pores that may be interconnecting to provide an interconnected porosity. Further details regarding this high energy beam ALM process are described in U.S. Prov. Pat. App. No. 62/517,456, hereby incorporated by reference herein in its entirety. To form the spring of the tissue attachment structure, a series of struts, which may be linear as in the example of FIGS. 1-3 or curvilinear, may be formed. Such struts may be flexible in the same or a similar manner as the struts of the flexible tubes described in U.S. Prov. Pat. App. No. 62/520,221, hereby incorporated by reference herein in its entirety, and may be built to extend from a substrate, e.g., the prosthesis, as also described in U.S. Prov. Pat. App. No. 62/520,221. To increase flexibility, the struts may be formed with a reduced thickness along at least a portion of their length. Of course, when ALM is used for multiple components of the prosthetic bone implant, any combination of the above technologies and approaches may be used to form a desired structure.

ALM may be used to form an entire prosthetic bone implant or any number of its constituent parts. In some examples, an ALM process is used to form either the prosthesis or the tissue attachment structure alone. In others, single components of the tissue attachment structure may be formed using an ALM process. In still further examples, the prosthesis and the tissue attachment structure are both formed together through an ALM process to create a monolithic, inseparable, structure. When ALM is used to form individual components of the prosthetic bone implant, such components may be assembled together after each component is formed.

Materials used to form the various components described above with an ALM process include, but are not limited to, metals (e.g., metal powder) that may be any one or any combination of titanium and its alloys, stainless steel, magnesium and its alloys, cobalt and its alloys including cobalt chromium alloys, nickel and its alloys, platinum, silver, tantalum niobium, and other super elastic materials such as copper-aluminum alloys. Non-metallic materials may also be used and include, but are not limited to, implantable plastics. These may be any one of or a combination of wax, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials such as collagen/cell matrices. To the extent other materials are described elsewhere in the specification, such materials are also contemplated for use in ALM processes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic bone implant comprising: a prosthesis; and a tissue attachment structure connected to the prosthesis, the tissue attachment structure comprising: a connective structure having a longitudinal dimension extending from a first end to a second end opposite the first end, the first and second ends of the connective structure being immovably connected to first and second attachment locations on the prosthesis, respectively, and at least part of the connective structure being separate from the prosthesis in between the first and second ends, at least a portion of the connective structure being continuous between the first end and the second end; and an interface structure connected to the connective structure at a first location on the interface structure and at a second location on the interface structure separate from the first location, the interface structure being positioned on a single side of a first plane coextensive with a central longitudinal axis of the connective structure along the longitudinal dimension, the interface structure configured for attachment of tissue thereto, wherein a length of the interface structure along a first direction parallel to the central longitudinal axis is less than a length of the prosthesis along the first direction, wherein the connective structure changes in shape when the interface structure is subject to tension, and wherein the first and second ends of the connective structure are separate from the first and second locations on the interface structure, and wherein the connective structure is connected to the prosthesis at the first and second attachment locations when the interface structure is subject to tension and when the interface structure is not subject to tension.

2. The prosthetic bone implant of claim 1, wherein the prosthesis includes a first surface and a second surface recessed relative to the first surface, the first and second attachment locations being below the first surface.

3. The prosthetic bone implant of claim 2, wherein the first end of the connective structure is attached to the first attachment location at a first wall of the prosthesis separating the second surface from the first surface and the second end of the connective structure is attached to the second attachment location at a second wall of the prosthesis separating the second surface from the first surface.

4. The prosthetic bone implant of claim 1, wherein the first and second locations on the interface structure are between the first and second ends of the connective structure.

5. The prosthetic bone implant of claim 1, wherein a portion of a surface of the interface structure in between the first and second locations is parallel to the plane and the interface structure is configured to move relative to the prosthesis when the interface structure is subject to tension, the interface structure returning to its original position relative to the prosthesis when the tension applied to the interface structure is removed.

6. The prosthetic bone implant of claim 1, wherein the connective structure is a spring or an auxetic structure.

7. The prosthetic bone implant of claim 1, wherein the interface structure includes a first material layer and a second material layer connected to the first material layer, the first material layer configured for attachment of tissue thereto and having greater porosity than the second material layer.

8. A prosthetic bone implant comprising:
a prosthesis; and
a tissue attachment structure connected to the prosthesis, the tissue attachment structure comprising:
a connective structure including a first spring, the first spring being connected to the prosthesis and having a longitudinal dimension extending from a first end to a second end opposite the first end; and
an interface structure connected to the first spring at a first location on the interface structure and at a second location on the interface structure separate from the first location, the interface structure being positioned on a single side of a first plane coextensive with a central longitudinal axis of the first spring of the connective structure along the longitudinal dimension, the interface structure being configured for attachment of tissue thereto,
wherein a length of the interface structure along a first direction parallel to the central longitudinal axis is less than a length of the prosthesis along the first direction,
wherein the connective structure changes in shape when the interface structure is subject to tension, and
wherein the first and second ends of the first spring are connected to the prosthesis at fixed locations on the prosthesis, the first spring remaining connected to the prosthesis at the fixed locations irrespective of a degree of tension applied to the interface structure.

9. The prosthetic bone implant of claim 8, wherein the first spring is connected to the prosthesis at the first end of the first spring and at the second end of the first spring, the first and second locations on the interface structure being in between the first and second ends of the first spring.

* * * * *